United States Patent
Sang et al.

(10) Patent No.: US 9,427,382 B2
(45) Date of Patent: Aug. 30, 2016

(54) METHOD AND COMPOSITION FOR ADHERING TO TOOTH STRUCTURE

(75) Inventors: Junjie Sang, Newark, DE (US); Paul D. Hammesfahr, Wyoming, DE (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 12/900,526

(22) Filed: Oct. 8, 2010

(65) Prior Publication Data

US 2011/0165539 A1    Jul. 7, 2011

Related U.S. Application Data

(63) Continuation of application No. 12/231,928, filed on Sep. 8, 2008, now abandoned, which is a continuation of application No. 11/700,461, filed on Jan. 31, 2007, now abandoned, which is a continuation of application No. 10/945,453, filed on Sep. 20, 2004, now abandoned, which is a continuation-in-part of application No. 09/107,913, filed on Jun. 30, 1998, now abandoned, and a continuation of application No. 10/117,252, filed on Apr. 5, 2002, now abandoned.

(51) Int. Cl.
| | |
|---|---|
| A61C 5/00 | (2006.01) |
| A61C 5/11 | (2006.01) |
| A61K 6/08 | (2006.01) |
| C08J 3/28 | (2006.01) |
| A61K 6/00 | (2006.01) |
| A61K 6/083 | (2006.01) |
| C08L 33/00 | (2006.01) |
| A61K 6/05 | (2006.01) |

(52) U.S. Cl.
CPC ............. *A61K 6/083* (2013.01); *A61K 6/0023* (2013.01); *A61K 6/05* (2013.01)

(58) Field of Classification Search
CPC ...... A61K 6/05; A61K 6/0023; A61K 6/083; C09J 4/00; C09J 123/00; C09J 129/00; C09J 131/06
USPC .................. 523/115, 116, 118; 524/365, 379
See application file for complete search history.

(56) References Cited

U.S. PATENT DOCUMENTS

| | | | |
|---|---|---|---|
| 4,499,251 A | 2/1985 | Omura et al. | |
| 4,514,342 A | 4/1985 | Billington et al. | |
| 4,514,343 A | 4/1985 | Cramer et al. | |
| 4,515,930 A | 5/1985 | Omura et al. | |
| 4,537,940 A | 8/1985 | Omura et al. | |
| 4,540,722 A | 9/1985 | Bunker | |
| 4,544,467 A | 10/1985 | Bunker et al. | |
| 4,645,456 A | 2/1987 | James | |
| 4,657,941 A | 4/1987 | Blackwell et al. | |
| 4,669,983 A | 6/1987 | Bunker | |
| 4,670,576 A | 6/1987 | Bunke | |
| 4,719,149 A | 1/1988 | Aasen et al. | |
| 4,855,475 A | 8/1989 | Bunker | |
| 4,872,936 A | 10/1989 | Engelbrecht | |
| 4,880,660 A | 11/1989 | Aasen et al. | |
| 4,929,746 A | 5/1990 | Bunker | |
| 4,959,297 A | 9/1990 | Palazzotto | |
| 4,966,934 A | 10/1990 | Huang et al. | |
| 5,089,051 A | 2/1992 | Eppinger et al. | |
| 5,177,121 A | 1/1993 | Bunker | |
| 5,256,447 A | 10/1993 | Oxman et al. | |
| 5,270,351 A | 12/1993 | Bowen | |
| 5,304,585 A | 4/1994 | Bunker | |
| 5,356,951 A | 10/1994 | Yearn et al. | |
| 5,362,769 A | 11/1994 | Waller et al. | |
| 5,367,002 A | 11/1994 | Huang et al. | |
| 5,401,783 A | 3/1995 | Bowen | |
| 5,498,643 A | 3/1996 | Antonucci et al. | |
| 5,530,038 A | 6/1996 | Yamamoto et al. | |
| 5,554,030 A | 9/1996 | Ario et al. | |
| 5,595,487 A | 1/1997 | Ario et al. | |
| 5,645,429 A * | 7/1997 | Blackwell ............ | A61K 6/0029 433/217.1 |

FOREIGN PATENT DOCUMENTS

| | | | |
|---|---|---|---|
| EP | 0237233 A2 | 9/1987 | |
| EP | 0321683 A1 | 6/1989 | |
| EP | 0323120 B1 | 7/1989 | |
| EP | 0329268 A2 | 8/1989 | |
| EP | 0347711 B1 | 12/1989 | |
| EP | 0393617 A2 | 10/1990 | |
| EP | 0408357 A2 | 1/1991 | |

(Continued)

OTHER PUBLICATIONS

Restorative Dentistry Techniques, Bonding fresh amalgam using Scotchbond Multi-Purpose Plus dental adhesive system by 3M dental Products Div.
Watanabe, L.G., et al, in Journal of Dental Research, 76 (Special Edition) Abs. 1398, 1977.
Hammesfahr, Paul, et al; Dental Materials, vol. 3;185, 1987.

*Primary Examiner* — Randy Gulakowski
*Assistant Examiner* — Christopher M Rodd
(74) *Attorney, Agent, or Firm* — Leana Levin; Douglas J. Hura; David A. Zdurne

(57) ABSTRACT

A dental adhesive composition has an adhesive component and an activator component. The adhesive composition has a volatile organic solvent component, one or more polymerizable (meth)acrylate compounds optionally containing fillers, and a polymerization photoinitiator. The adhesive component may also be a substantially homogeneous mixture of one or more polymerizable (meth)acrylate compounds and an effective amount of a photoinitiator, without a solvent. The activator component includes an aromatic sulfinate salt and an activator component solvent. A method for adhering a restorative to a dental surface includes preparing the surface for restoration; applying a mixture of an adhesive component and an activator component to the prepared cavity, thereby forming a coated cavity surface; and, applying a direct or indirect dental restorative to the coated cavity surface.

9 Claims, No Drawings

(56) References Cited

FOREIGN PATENT DOCUMENTS

| EP | 0423430 | B1 | 4/1991 |
|---|---|---|---|
| EP | 0661034 | A1 | 7/1995 |
| EP | 0980233 | B1 | 11/2005 |
| WO | 9600558 | A1 | 1/1996 |
| WO | 9600559 | A1 | 1/1996 |

* cited by examiner

METHOD AND COMPOSITION FOR ADHERING TO TOOTH STRUCTURE

RELATED APPLICATIONS

This application is a continuation of U.S. Ser. No. 12/231,928 with a filing date of Sep. 8, 2008, now abandoned, which is a continuation of Ser. No. 11/700,461 with a filing date of Jan. 21, 2007, now abandoned, which is a continuation of U.S. Ser. No. 10/945,453 with a filing date of Sep. 20, 2004, now abandoned, which is a continuation of U.S. Ser. No. 10/117,252 with a filing date of Apr. 5, 2002, now abandoned, which is a continuation-in-part of U.S. Ser. No. 09/107,913 with a filing date of Jun. 30, 1998, now abandoned.

TECHNICAL FIELD

The invention relates to adhesion of dental restoratives to teeth, porcelain, metals, amalgams and other dental surfaces. The invention provides a method and composition for adhering to such dental surfaces. Specifically, the inventive compositions include a (meth)acrylate adhesive component optionally containing one or more fillers, and a sulfinate salt activator component. The method according to the invention includes preparing the dental surface, applying the inventive material and then applying a dental restorative according to appropriate direct or indirect dental restoration procedures.

BACKGROUND OF THE INVENTION

It is most desirable, when filling a tooth cavity with a filling material, such as a polymerizable dental restorative, to ensure good adhesion between the tooth surrounding the cavity and the set (polymerized) filling material since there is thereby obtained a good seal between the set filling material and the tooth which prevents, or at least markedly inhibits, ingress of mouth fluids and bacteria into the filled cavity and thus prevents further decay or loss of the filling material. In order to achieve good adhesion between the filling material and the tooth tissues, enamel or dentin, it has been recommended to provide a primer or adhesive bonding layer intermediate to the filling material and surfaces of a prepared tooth. The filling material is normally an amalgam or non-amalgam materials for direct or indirect restorations.

The priming compositions heretofore known in the art, require the separate steps of applying a priming material to a prepared dental surface, followed by the application of a dental adhesive. Such a method is described for example, in U.S. Pat. No. 5,595,487 and in U.S. Pat. No. 5,554,030. In practice, it has been found that such multi-step procedures are laborious and time consuming. The dental clinician requires time effective procedures. Hence, use of these procedures has been undesirable.

A need exists therefore, for a dental composition which will simultaneously provide a priming and adhesive material intermediate to the prepared dental surface and the subsequently applied restorative material in both direct and indirect dental procedures. By "direct" it is meant a dental procedure where a tooth is prepared to receive a dental restorative composition which is formed and hardened in place. An "indirect" procedure is one wherein a dental construct such as an inlay, only, bridge, crown or the like is first prepared and then set into the prepared and adhesive-coated tooth.

OBJECTS OF THE INVENTION

It is an object of the present invention to provide a dental composition.

It is another object of the invention to provide such a composition which will enhance adhesion of a dental restorative material to a dental surface.

It is still another object of the invention to provide a dental composition as above, which is applied as a mixture or as a single composition.

It is a further object of the invention to provide a method of restoring a tooth structure.

It is an additional object of the invention to provide a method as above, which does not require separate steps for applying a priming component and an adhesive component.

These and other object of the invention, which will become apparent from the disclosure and claims to follow, are carried out by the invention as hereinafter described and claimed.

SUMMARY OF THE INVENTION

A dental adhesive composition according to the invention comprises from about 5 to about 80 percent by weight of an adhesive or adhesive/primer component optionally containing one or more fillers, and from about 20 to about 95 percent by weight of an activator component; the adhesive component comprising at least about 35 percent by weight of a volatile organic solvent component, at least about 5 percent by weight of one or more polymerizable (meth)acrylate compounds, and an effective amount of a polymerization photoinitiator; the polymerizable (meth)acrylate compound being substantially soluble or homogeneously dispersed in said volatile organic solvent component.

The adhesive component can also comprise at least about 5% by weight of one or more (meth)acrylate compounds and an effective amount of a photoinitiator. The adhesive is a substantially homogeneous mixture of the above compounds but in the absence of said volatile organic solvent(s).

The activator component comprising from about 0.1 to about 10 percent by weight of an aromatic sulfinate salt and from about 90 to about 99.9 percent by weight of an activator component solvent. The activator component may optionally contain additives that promote self-cure and/or light cure interactions between the adhesive compositions and the restoratives.

A method according to the invention, for adhering a non-amalgam dental restorative to a dental surface, comprises the steps of:
a) Preparing the dental surface for restoration, including direct and/or indirect restoration;
b) Optionally etching the surface with an acid;
c) Applying a mixture of an adhesive component and an activator component to the prepared surface, thereby forming a coated dental surface; and,
d) Applying a non-amalgam dental restorative to the coated dental surface. It is an aspect of the invention that step (c) may include applying the adhesive component and the activator component sequentially rather than mixing them first.

A method according to the invention for adhering an amalgam dental restorative to a dental surface, comprises the steps of:
a) Preparing the surface for restoration;
b) Optionally etching the surface with an acid;
c) Applying a mixture of an adhesive component and an activator component to the prepared surface (or sequentially applying these two components), thereby forming a coated dental surface;

d) Optionally applying a chemically curable dental adhesive to said coated dental surface, wherein the chemically curable adhesive includes an oxidizing agent and a reducing agent; and, e) Applying an amalgam dental restorative to the coated dental surface.

PREFERRED EMBODIMENTS FOR CARRYING OUT THE INVENTION

The dental adhesive composition according to the invention is a mixture of an adhesive component and an activator component. It is to be understood that by "adhesive" it is meant either an adhesive or a primer/adhesive component. As will be discussed below, the adhesive component may include a solvent (the primer/adhesive) or it may be a resin adhesive which is solvent-free. The term "adhesive" will be understood to include all such adhesive systems.

One preferred composition has from about 5 to about 80 percent by weight of the adhesive component and from about 20 to about 95 percent by weight of the activator component. The composition may also contain fluoride.

The inventive materials my be provided as a single composition, all components being packaged in one bottle for subsequent use, or as a "mixed" system wherein the adhesive component is packaged separately from the activator component, the two being mixed at the same time of use and before being used in the inventive method. Both such packaging applications are within the scope of the invention.

The adhesive component preferably includes at least about 35 percent by weight of a solvent such as water, a volatile organic solvent, or mixtures thereof, and at least about 5 percent by weight of one or more polymerizable (meth)acrylate compounds, the remaining components to form 100 percent by weight of the adhesive component being initiators or other cure components, polymerizable monomers and oligomers, polymerizable phosphates or other ethylenically unsaturated components, other optional fillers, fluoride release compounds, stabilizers and the like. An example of a useful fluoride release compound is cetylamine hydrofluoride.

The adhesive component may optionally contain a filler including any filler that is useful in dental applications. For example, an inorganic filler such as silanated inorganic silica may be employed. Another example is a sol-gel inorganic/organic nano-scale composite. A prepolymerized organic filler may also be employed.

The adhesive component preferably includes an effective amount of a photopolymerization initiator. The polymerizable (meth)acrylate compounds should be substantially soluble or substantially homogeneously dispersed in the selected solvent or solvents, and are polymerizable to form a polymeric material. Certain filler materials may no necessarily be soluble in the solvent(s) and as such are preferably substantially homogeneously dispersed in the adhesive component.

Examples of useful solvents for the adhesive component include ethanol, methanol, isopropanol, dimethyl ketone, ethylmethyl ketone, water, and the like, as well as mixtures thereof. The adhesive component according to the present invention may also be a solvent-free adhesive resin, as discussed above.

Preferred polymerizable methacrylate compounds include for example, those monomers having a solubility in water of less than about 5%, and more preferably have a solubility in water of less than about 1%. Other useful polymerizable (meth)acrylate compounds include multifunctional polymerizable compounds having at least three (meth)acrylate moieties and a phosphate moiety. Still further preferred monomers include surface active monomers having acid functional groups and containing (meth)acrylates. Examples of useful acid functional groups include maleic acid, phosphonic acid, carboxylic acid, sulfonic acid, and mixtures thereof.

Exemplary monomers include diethylene glycol dimethacrylate; triethylene glycol dimethacrylate; tetraethylglycol dimethacrylate; glycerol-1,2-dimethacrylate; glycerol-1,3-dimethacrylate; the reaction product of butanediol diglycidyl ester and methacrylic acid; tetrahydrofurfural methacrylate; methacryloxyethyl maleic ester; methacryloxyethyl succinate; urethane dimethacrylate; Bis-GMA (Bis-phenol A Glycydyl Methacrylate, also known as 2,2-bis[4-(2-hydroxy-3-methacyloyloxypropoxy)phenyl] propane); trimethylolpropane tri(meth)acrylate; Ethoxylated bisphenol-A dimethacrylate; bisphenol-A dimethacrylate; and, mixtures thereof. Monomers having a solubility in water higher than 5% are less preferred but still within the scope of the invention. Monomers having a solubility in water less than about 1% are more preferred. Highly water soluble monomers such as hydroxyethyl methacrylate and hydroxypropyl methacrylate tend to provide lower adhesion and are less suitable for use in compositions of the invention.

An example of a useful urethane dimethacrylate is 7,7,9,63,65 hexamethyl-4,13,60,69-tetra-oxo-3,14,19,24,29,34,39,44,49,54,59,70-dodecanaoxa-5,12,61,68-tetra-azadoheptacontane-1,72 diyldimethacrylate, also known as urethane dimethacrylate resin.

A volatile solvent is removed after application of the adhesive and/or primer/adhesive to the dentine, enamel, metal or other dental surface. The monomer is preferably less volatile than the solvent.

Examples of useful photoinitiators include those useful in dental applications, including camphorquinone, diaryliodium metal complex salts, chromophore-substituted halomethyl-s-triazines, organo-phosphine oxide (preferably α-cleavage type phosphineoxide), and halomethyl oxadiazoles, and others conventional in the art, such as those disclosed in U.S. Pat. Nos. 5,595,487; 4,514,342; and 4,514,343 which are incorporated by reference for such disclosure, as well as mixtures thereof. An effective amount of such an initiator is employed, as will hereinafter be exemplified.

The activator component preferably comprises from about 0.1 to about 10, more preferably about 0.5 to about 5, more preferably still about 0.5 to about 3, percent by weight of a sulfinate salt and from about 90 to 99.9, more preferably from about 95 to about 99.5, even more preferably about 97 to about 99.5, percent by weight of an activator component solvent, and optionally a reducing agent such as N,N-bis-(2-hydroxyethyl)-p-toluidine (DHEPT). Examples of useful activator component solvents include acetone, ethanol, water, dimethyl sulfoxide (DMSO), methylene chloride, chloroform, and the like, as well as mixtures thereof.

Preferred sulfinate salts are aromatic, having the general structure

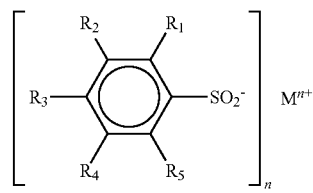

wherein R1-R5 are individually a hydrogen or an alkyl group having from 1 to about 6 carbon atom, preferably hydrogen or a methyl group in the para-position; M is a cation; and "n" is an integer being 1 to 4. Preferred examples of Mn+ are sodium, calcium, ammonium, potassium or lithium. Para-toluene sodium or lithium sulfinate and benzene sodium or lithium sulfinate are preferred salts.

The dental adhesive composition as described hereinabove is employed in inventive methods for restoring teeth. A method according to the invention, for adhering an amalgam or non-amalgam dental restorative to a dental surface, includes: (a) preparing the dental surface for restoration; (b) optionally etching the surface with an acid; (c) applying a mixture of an adhesive component and an activator component to the prepared surface, thereby forming a coated dental surface; and, (d) applying an amalgam or non-amalgam dental restorative to the coated dental surface. As an alternative, in step (c), the adhesive and the activator components may be applied sequentially instead of being first mixed. It will also be appreciated that the order of the method steps according to the invention may be varied as appropriate. The inventive methods and compositions are useful with direct and indirect dental procedures. Further, in step (a), it is understood that "preparing the dental surface for restorations" includes preparing the surface for both direct and indirect restorations without limitation.

The step of preparing the dental surface, which may be a cavity or the like, includes conventional techniques such as removing decayed or otherwise damaged portions by mechanical, abrasive, laser or other means. The surface can then be cleaned by washing or other techniques.

To enhance mechanical retention of the restorative material to the dental surfaces, the tooth surface may optionally be etched whereas the indirect restoration surface may be sandblasted and/or silanated and/or acid etched where applicable according to conventional techniques. Any other conventional preparation technique is also within the scope of the invention. Etching is well known in the art, and any etching technique is also within the scope of the invention. For example, etching may be completed by applying an acid such as phosphoric acid to the prepared dental surface. The etching acid is normally removed by washing and/or drying.

The mixture of an adhesive component and an activator component as used in the inventive method, is selected from those inventive dental compositions as discussed hereinabove. It is applied to the surface to provide a coated dental surface.

If employing a non-amalgam type restorative material, such as PrismaTPH Spectrum composite or EnFOrce WF Composite Resin Luting Cement, both available from Dentsply International Inc. (L.D. Caulk Division), the restorative may be applied to the coated dental surface. If the restorative is an amalgam material, such as Dispersalloy (admixed alloy) or Megalloy (spherical alloy) both available from Dentsply International Inc. (L.D. Caulk Division), it is sometimes optionally useful to first apply a chemically curable adhesive to the coated dental surface followed by application of the amalgam restorative. Preferred chemically curable adhesives include for example, Amalgam Bonding Base and Catalyst available from Dentsply International Inc. (L.D. Caulk Division). Such chemically curable adhesives contain an oxidizing agent such as benzoyl peroxide, and a reducing agent such as N,N-bis-(2-hydroxyethyl)-p-toluidine (DHEPT). It will be appreciated that this step of applying a chemically curable adhesive when using an amalgam restorative is preferred but is optional.

GENERAL EXPERIMENTAL

In order to exemplify the inventive compositions, a dental composition as above was prepared. The activator component was a substantially homogeneous mixture of 0.6 percent by weight of para-toluene sodium sulfinate, 79.5 percent by weight of dimethyl ketone and 19.9 percent by weight of ethanol, to form 100 percent by weight of the activator component. The adhesive component was Prime & Bond® 2.1 (abbreviated P&B below) from Dentsply International Inc., known to contain about 50-80 percent by weight of solvent, about 5-15 percent by weight of multifunctional polymerizable compounds having at least three (meth)acrylate moieties and phosphate moiety, and the balance being other (meth)acrylate monomers and oligomers, one or more fluoride release compounds, and other additives. The activator and adhesive components were used in approximately a 1:1 mixture by volume, and this mixture is discussed below as the "inventive composition".

Example 1

This inventive composition was tested for shear bond strength (SBS) using a Single Plane Shear Test Assembly apparatus (SPSTA) as described by L. G. Watanabe, et al., in Journal of Dental Research, 76 (Special Edition) Abs. 1398, 1977 and/or other standard compressive shear bond strength test methods as described in U.S. Pat. No. 5,645,429 which is hereby incorporated by reference for such disclosure, and for example, in Dental Materials, vol. 3; 185, 1987 by Hammesfahr et al. The compositions tested included self curing (SC) and light curing (LC or VLC for "visible light cure") materials. Further, the inventive materials were tested with etching or non-etching to dental surfaces as will be noted below, and were also compared to various commercially available adhesive products. As will be shown in the following tables, the inventive material shows comparable or improved results over the commercially available products. "SD" as used below is standard deviation, and "Del." Is dentin or enamel delamination. Cohesive failure as reported indicates bond fracture occurred within either tooth substrate dentin or enamel or restoratives and are reported as the number of failures (F) per the total number tested (T) (F/T). Both immediate (15 minute) and 24-hour bond strength of different composite resin luting cements to human dentin using the inventive composition or other commercially available dual-cure adhesive systems were evaluated by SPSTA test methods as described above. The results are summarized in TABLE 1.

TABLE I

System Comparison* of The Inventive Composition
Immediate (15 minute) and 24 Hours Shear Bond Strength**

| Dual-Cure Universal Dental Adhesive Systems | Immediate SBS (MPa) | | 24 Hrs SBS (MPa) | | Comments |
|---|---|---|---|---|---|
| | X ± SD, Dentin Del | (%) | X ± SD, Dentin Del | (%) | |
| Dual-Cure Prime & Bond ™ 2.1 (Denisply/Caulk) | 6.72 ± 2.38 (total SC) | 20% | 10.32 ± 1.75 ≥13.97 ± 0.96 | | 40% total SC 100% Enforce LC 1' |
| | 8.53 ± 1.98 (total SC) | 0% | 15.47 ± 2.27 ≥13.67 ± 2.64 | | 75% Primers LC 10" 100% LC both Primers and Enforce |
| SBMP+ (3M) | 4.98 ± 1.00 | 20% | 6.36 ± 2.71 8.98 ± 3.05 | | 20% total SC (per DFU) 0% LC 10" Activator/Primer |
| All-Bond 2 (BISCO, Inc.) | 9.15 ± 0.73 | 60% | 11.89 ± 2.91 | | 80% Primers LC 20" (per DFU) |

TABLE I-continued

System Comparison* of The Inventive Composition
Immediate (15 minute) and 24 Hours Shear Bond Strength**

| Dual-Cure Universal Dental Adhesive Systems | Immediate SBS (MPa) X ± SD, Dentin Del (%) | 24 Hrs SBS (MPa) X ± SD, Dentin Del (%) | Comments |
|---|---|---|---|
| OptiBond (Ker) | 8.22 ± 3.70  0% | 7.68 ± 1.72  0% | Nexus Cement LC 1' (per DFU) |

*All the test samples for different system were prepared according to the manufacturer's directions for use (DFU), and the manufacturer's recommended resin cement was used for different system, i.e. the inventive composition/EnForce WF (Caulk), SBMP+/3M Resin Cement (3M). All-Bond 2/Duo-Link (BISCO, Inc.), and OptiBond/Nexus (Kerr).
**SBS was tested using Single Plane Shear Test Assembly.

As indicated by the SBS data, the inventive composition, two-bottle dual-cure dental adhesive system showed equivalent (or improved) bonding performance to competitors' multi-bottle dental adhesive system (3M's SBMP+, Bisco's All-Bond and Kerr's OptiBond), with the additional advantages of simplicity, i.e. simple technique, less total application time, time/cost saving, fluoride-release, thin-film thickness, and the like.

Example 2

Using the SPSTA test method, bond strength of different restorative materials to human teeth (dentin) using the inventive composition was evaluated and the results are shown in TABLE II.

TABLE II 24 hr. Shear Bond Strength of Different Restoratives to Human Teeth Using The Inventive Composition

| BONDING SUBSTRATE | SURFACE TREATMENT | Inventive Composition | RESTORATIVES | 24 Hour Shear Bond Strength (MPa) | |
|---|---|---|---|---|---|
| Dentin | Etched | Self Cure (SC) | SC Enforce ™ WF | 11.20 ± 2.58 | 80% |
| Dentin | Etched | Visible Light Cure (VLC) | SC Enforce ™ WF | 13.93 ± 1.81 | 75% |
| Dentin | Etched | Visible Light Cure (VLC) | SC Enforce ™ WF | 15.47 ± 2.27 | 75% |
| Dentin | Etched | Visible Light Cure (VLC) | VLC Enforce ™ WF | ≥13.67 ± 2.64 | 100% |
| Dentin | Unetched | Self Cure (SC) | SC Enforce ™ WF | 4.18 ± 2.91 | 0% |
| Dentin | Unetched | Visible Light Cure (VLC) | SC Enforce ™ WF | 9.79 ± 3.0 | 60% |
| Dentin | Etched | Self Cure (SC) | SC FluoroCore ™ | 8.90 ± 3.0 | 33% |
| Dentin | Etched | Visible Light Cure (VLC) | VLC TPH ™ Spectrum Composite | 31.34 ± 3.82 | 10% |

As can be seen from the SBS results in TABLE II (and TABLE III below) the inventive composition can be used to adhere different restorative materials to tooth structure in a variety of direct and indirect restoration applications with good bonding performance.

Example 3

Using the SBS test method as described in Dental Materials, Vol. 3; 185, 1987, and in the incorporated U.S. Pat. No. 5,645,429, 24-hour enamel SBS of different restoratives used in direct and/or indirect restorations using the inventive composition was evaluated. The results are summarized in TABLE III.

TABLE III

24 Hour SBS* of Different Restoratives to Human Tooth Using the Inventive Composition

| BONDING SUBSTRATE | SURFACE TREATMENT | INVENTIVE COMPOSITION | RESTORATIVES | 24 Hrs. SBS (MPa) X ± SD: Enamel Del (%) | |
|---|---|---|---|---|---|
| Enamel | Etched | Self Cure (SC)[1] | SC Enforce ™ WF[1] | 26.8 ± 4.7 | 100% |
| Enamel | Etched | Visible Light Cure[2](VLC) | VLC Enforce ™ WF[2] | 23.7 ± 4.8 | 100% |
| Enamel | Etched | Visible Light Cure[3](VLC) | VLC TPH ™ Spectrum Composite[3] | 31.0 ± 8.0 | 80% |

*SBS was tested using Caulk's Compressive Shear Bond Strength Test Method
[1]Bonding Protocol-1(total SC): Etched Enamel (Caulk 34% tooth gel/15")/P&B 2.1 & SC Activator (I/Ipremix)[IC/wet, NC]/Enforce(SC)
[2]Bonding Protocol-2: Etched Enamel (Caulk 34% tooth gel 15")/P&B 2.1 & SC Activator (I/Ipremix)[IC/wet, LC 10"]/Enforce(LC 40")
[3]Bonding Protocol-3: Etched Enamel (Caulk 34% tooth gel 15")/P&B 2.1 & SC Activator (I/I premix)[IC/wet, LC 10"]/TPH Spectrum (LC40")

As indicated by the 24 hour enamel SBS data in TABLE III, the inventive composition as a 2-bottle dual cure dental adhesive system showed very good bonding performance (up to 31 MPa, with 100% cohesive failure within human enamel) to human enamel (even in total self cure mode) in relevant to direct and indirect dental applications.

Example IV

Using the SBS test method as in Example III, except that a porcelain substrate is used in place of human enamel, 24 hour SBS of Enforce Resin Cement to an all-ceramic substrate (commercially available from DENTSPLY International Inc.) using the inventive composition was tested. The obtained results are shown in TABLE IV, indicated that the inventive composition can be used to adhere to porcelain substrate with high blood strength.

TABLE IV

24 Hour SBS* of Enforce WF (B1) Cement to All-Ceramic Substrate Using the Inventive Composition

| Bonding Substrate | Bonding Protocol | X ± SD; # Cob (MPa) |
|---|---|---|
| Porcelain | Control: substrate porcelain (microetched w/50 μm alumina, then silanated per DFU)/Enforce WF [B1](I/I)(LC) | 12.5 ± 3.9; 0/6 |
| Porcelain | Substrate porcelain (microetched, then silanated per DFU)/P&B 2.1 & SCA (I/I mix) [C/NC]/Enforce WF [B1](I/I)(SC) | 14.8 ± 4.1; 0/7 |
| Porcelain (Substrate porcelain) | Substrate porcelain (microetched, then silanated per DFU)/P&B 2.1 & SCA (I/I mix) [C/LC]/ Enforce WF [B1](I/I)(LC) | 25.0 ± 6.6; 6C/6 |
| Porcelain (Substrate porcelain) | Substrate porcelain (Microetched, HF etched/60", then silanated)/ Enforce WF [B1](I/I)(LC) | 11.1 ± 5.0; 4C/5 |
| Porcelain (Substrate porcelain) | Substrate porcelain (Microetched, HF etched/60", silanated)/ P&B 2.1(I/I mix)[C/NC]/Enforce WF [B1](I/I)(SC) | 20.7 ± 3.51 5C/5 |

*SBS was tested using Caulk's Compressive Shear Bond Strength Test Method.

Example V

Using the same test method as in Example IV, the inventive composition was evaluated for simulating a clinical "Maryland Bridge" application. The results are shown in TABLE V. These data show the inventive composition can also be used to strongly bond non-precious metals (rexillium III) in human enamel in relevant clinical applications.

TABLE V 24 hr. SBS of Non-Precious Metal (Rexillium III) to Etched Human Enamel Using the Inventive Composition and Enforce WF (Opaque)*

| Bonding Substrate | Bonding Protocol | X ± SD (MPa) | Fracture Mode |
|---|---|---|---|
| Enamel | Enamel (34% Gel/30")/Prime & Bond 2.1 & SC Activator (IC/wet, NC)/ Enforce w/F [OP](I/I) (IL, SC 6', LC 3 × 20")/ Rex III[microetched, Prime & Bond 2.1 & SC Activator (IC/wet, LC 10")] | 23.2 ± 15.4 (SC mode) | 33% enamel cob. Fail, others adh/ cob mixed. |
| Enamel | Enamel (34% Gel/30")/Prime & Bond 2.1 & SC Activator (IC/wet, LC 10")/ Enforce w/F [OP](I/I) (IL, SC 6', LC 3 × 20")/ Rex III[microetched, Prime & Bond 2.1 & SC Activator (IC/wet, LC 10")] | 13.1 ± 9.4 (Add LC) | Mixed failure (Cement) Cob/adh. |

*SBS was tested by Caulk's Compressive Shear Bond Strength Test Method where 3.15 mm Rexillium III Post used Example VI Using the SPSTA test method the inventive composition was evaluated for its adhesive amalgam bonding application in comparison with several commercially available adhesive systems. The obtained amalgam bond strength to dentin data is summarized in TABLE IV. As indicated by these data, the inventive composition showed acceptable adhesive bonding performance.

TABLE VI

24 Hour Shear Bond Strength* of Fresh Amalgam with Human Dentin

| Sample | Bonding Protocol | X(SD), #Del. |
|---|---|---|
| Prime & Bond ® 2.1 Final Cure Adhesive | Etched dentin(Caulk gel/15")/P&B 2.1&SC Activator (I/I premix)[IC/wet, NC]/Caulk SC Bonding Agent Base/catalyst (I/I equal drop mix)[IL, SC]/Dispersalloy ® amalgam | 4.1 (1.3), 0/5 |
| SBMP+ | Etched dentin(3M etching/15")/Activator/Primer[IC, NC]/Adhesive & Catalyst (I/Imix)[1 Thin Layer, SC]/Dispersalloy ® amalgam Per DFU | 2.2 (0.9), 0/5 |
| SBMP+ | Repeat amalgam bonding, per DFU | 3.7 (0.2), 0/5 |
| OptiBond ® | Per DFU: Etched (Kerr's etching/15")/Primer$$[C/serub 30", NC]/Adhesive 2[$$ thin Layer; LC 30"]/Dispersalloy ® amalgam | 1.8 (1.9), 0/5 |
| All Bond ® 2 | Per DFU: Etched dentin(Uni-Etch/15")/Primer P&B(I/I mix)[5C, LC20"]/Pre Bond&D/E Bond (I/I mix)[Thin Layer, SC]/Dispersalloy ® amalgam | 2.6 (1.8), 0/5 |
| Amalgam Bond Plus w/HPA | Unetched dentin/Activator/ahd. Agent/Mix (base/cat/HPA)[IL, SC]/Dispersalloy ® amalgam Per DFU | 6.5 (1.7), 0/5 |
| Amalgam Bond Plus w/o HPA | Unetched dentin/Activator/adh.agent/Mix (base&cat)[IL, SC]/Dispersalloy ® amalgam | 2.4 (1.8), 0/5 →1.7 (0.6), 0/5 ←(repeated BS) |

*SBS was tested using Single Plane Shear Test Assembly

It is apparent therefore, that the dental compositions as described herein are effective in carrying out the objects of the invention. While the principles of the invention have been made clear by the illustrative embodiments discussed, those skilled in the art will appreciate that modifications to composition components including the addition of other components to the composition for promoting chemical or photocure polymerization, amounts, grades, process and method conditions and the like, can be made and still fall within the scope of those principles and of the invention.

It is claimed:

1. A dental adhesive composition comprising:
   a. from about 5 to about 80 percent by weight of an adhesive component comprising:
      (i) at least 35 percent by weight of a volatile organic solvent component;
      (ii) at least about 5 percent by weight of three polymerizable (meth)acrylate compounds selected from the group consisting of trimethylolpropane tri(meth)acrylate, diethylene glycol dimethacrylate, and 7,7,9,63,65-hexamethyl-4,13,60,69-tetra-oxo-3,14,19,24,29,34,39,44,49,54,59,70-dodecanaoxa-5,12,61,68-tetra-azadoheptacontane-1,72 diyldimethacrylate;
      (iii) an effective amount of a polymerization initiator; and
      (iv) optionally a filler component; and
   b. from about 20 to about 95 percent by weight of an activator component comprising:
      (i) from about 0.1 to about 10 percent by weight of an aromatic sulfinate salt elected from para-toluene sodium sulfinate, para-toluene lithium sulfinate, benzene lithium sulfinate or mixtures thereof, and
      (ii) from about 90 to about 99.9 percent by weight of an activator component solvent;
   wherein the adhesive component further comprises a multifunctional polymerizable compound having at least three (meth)acrylate moieties and a phosphate moiety;
   wherein said adhesive solvent component is selected from the group consisting of ethanol, methanol, isopropanol, dimethyl ketone, ethylmethyl ketone, water, and mixtures thereof;
   wherein said activator component solvents is selected from the group consisting of acetone, ethanol, water, dimethyl sulfoxide (DMSO), methylene chloride, chloroform, and mixtures thereof;
   wherein said initiator is a photoinitiator that is selected from the group consisting of camphorquinone, diaryliodium metal complex salts, chromophore-substituted halomethyl-s-triazines, phosphine oxide, halomethyl oxadiazoles, and mixtures thereof;
   wherein said dental adhesive composition further comprises:
      a fluoride release agent; and
      a cure additive selected from the group consisting of self-cure and light cure additives and mixtures thereof, such that said additive promotes cure interactions between the composition and a restorative material.

2. A composition as in claim 1, wherein said three polymerizable (meth)acrylate compound is substantially soluble in said solvent component.

3. A composition as in claim 1, wherein said initiator is a photoinitiator.

4. A method according to the invention, for adhering a non-amalgam dental restorative to a dental surface, comprises the steps of:
   a) preparing the dental surface for restoration;
   b) optionally etching the surface with an acid;
   c) applying the dental adhesive composition of claim 1 to the prepared surface, thereby forming a coated dental surface; and,
   d) applying a non-amalgam dental restorative to the coated dental surface.

5. A method as in claim 4, wherein the adhesive component of said dental adhesive composition is a substantially homogeneous mixture the three polymerizable (meth)acrylate compounds and an effective amount of a photoinitiator and optionally one or more fillers.

6. A method as in claim 4, wherein said three polymerizable (meth)acrylate compound are substantially soluble or substantially homogeneously dispersed in adhesive component (a) solvent component.

7. A method as in claim 4, wherein said step (c) includes applying said dental adhesive composition as a mixture of the adhesive component and the activator component.

8. A method as in claim 4, wherein said step (c) includes sequentially applying said dental adhesive composition as a mixture of the adhesive component and the activator component.

9. A method according to the invention for adhering an amalgam dental restorative to a dental surface, comprises the steps of:
   (a) preparing the surface for restoration;
   (b) optionally etching the surface with an acid;
   (c) applying the dental adhesive composition of claim 1 to the prepared surface, thereby forming a coated dental surface;
   (d) optionally applying a chemically curable dental adhesive to said coated dental surface, wherein the chemically curable adhesive includes an oxidizing agent and a reducing agent; and
   (e) applying an amalgam dental restorative to the coated dental surface.

* * * * *